United States Patent [19]
Sutcu et al.

[11] Patent Number: 5,637,111
[45] Date of Patent: Jun. 10, 1997

[54] BIPOLAR ELECTROSURGICAL INSTRUMENT WITH DESICCATION FEATURE

[75] Inventors: Maz Sutcu, New Hartford; John Gentelia, Madison; Frank Williams, Utica, all of N.Y.

[73] Assignee: Conmed Corporation, Utica, N.Y.

[21] Appl. No.: 467,163

[22] Filed: Jun. 6, 1995

[51] Int. Cl.[6] ................................................ A61B 17/39
[52] U.S. Cl. .......................... 606/51; 606/48; 606/50; 606/174
[58] Field of Search ................ 606/45, 46, 48–50, 606/51, 52, 174

[56] References Cited

U.S. PATENT DOCUMENTS

| | | |
|---|---|---|
| 3,651,811 | 3/1972 | Hildebrandt et al. . |
| 5,324,289 | 6/1994 | Eggers . |
| 5,330,471 | 7/1994 | Eggers ........................................ 606/50 |
| 5,352,222 | 10/1994 | Rydell . |
| 5,356,408 | 10/1994 | Rydell . |

*Primary Examiner*—Lee S. Cohen
*Attorney, Agent, or Firm*—Larson & Taylor

[57] ABSTRACT

A bipolar electrosurgical instrument including four shearing members is disclosed. The shearing members are movable to an open position for grasping tissue, a closed position for desiccating tissue by application of electrical current and a cutting position for shearing tissue. The electrical current may be applied in an X-shaped pattern to thereby localize desiccation to the maximum extent possible. A method of using the bipolar electrosurgical instrument is also disclosed.

13 Claims, 5 Drawing Sheets

BIPOLAR ELECTROSURGICAL INSTRUMENT WITH DESICCATION FEATURE

FIELD OF THE INVENTION

The invention relates generally to the design of a bipolar electrosurgical instrument. More particularly, the invention relates to electrosurgical scissors incorporating bipolar electrodes such that mechanical cutting and electrodesiccation are accomplished in an improved manner.

BACKGROUND OF THE INVENTION

The control of bleeding during surgery is an important issue. Electrosurgical techniques that pass a current through the patient's tissue between two electrodes for both cutting and causing hemostasis to tissue are known. The current passing through the tissue causes heating of the tissue as a function of the current density and the resistance of the tissue. Such heating causes the tissue proteins to form coagulum that seals the bleeding sites.

In bipolar electrosurgical devices, two electrodes are closely spaced together to thereby confine current flow locally to the tissue disposed between the electrodes. One difficulty encountered with prior art electrosurgical devices is that of controlling the current flow to the patient's tissue such that no undesirable trauma is brought about in adjacent tissue. Although bipolar electrosurgical devices have helped to localize current flow, these devices have yet to be optimized in this respect. Further, some of these devices present difficulties in selectively applying the current flow. Also, many of these devices are difficult to manufacture and have a limited durability and service life.

For example, U.S. Pat. No. 3,651,811 describes bipolar electrosurgical scissors having opposing cutting blades forming active electrodes. This device enables a surgeon to sequentially coagulate the blood vessels contained in the tissue and mechanically sever the tissue with the scissor blades. However, this device must be handled carefully in order to avoid a short circuit.

One proposed solution to this problem can be found in U.S. Pat. Nos. 5,352,222 and 5,356,408. These patents disclose bipolar electrosurgical scissors wherein each cutting blade includes a cutting surface, an electrically non-conductive layer and an electrically conductive outer surface which serves as the electrode.

However, these devices suffer from three important disadvantages. First, they require a three layer laminate which makes them difficult to manufacture. Second, the flow of electric current through the tissue is not sufficiently localized by these devices to prevent trauma to adjacent tissue since the current must flow from the back of one cutting blade element to the back of the other cutting blade element. Finally, since the current is not applied directly via the cutting surface, this device does not optimize cutting and desiccation.

Another bipolar electrosurgical cutting apparatus is disclosed in U.S. Pat. No. 5,324,289. In one embodiment disclosed in this patent, one of the cutting surfaces is made of a conductive material and serves as an electrode while the other cutting surface is covered by a coating of a non-conductive material. Thus, in this device, the current flows from the surface of one cutting edge to the back side of the other cutting edge. Accordingly, this device suffers from the same disadvantage as the previous device in that the flow of electric current is not sufficiently localized to prevent trauma to adjacent tissue and provide optimum cutting and desiccation.

Thus, a need exists for improvements in bipolar electrosurgical instruments in order to further localize current flow, reduce manufacturing costs and improve the overall efficiency of such devices.

OBJECTS OF THE INVENTION

It is the primary object of the present invention to provide a bipolar electrosurgical instrument which localizes the flow of current to a greater extent than prior art devices.

It is a further object of the present invention to provide a bipolar electrosurgical instrument which is easy to manufacture.

It is a still further object of the present invention to provide a bipolar electrosurgical instrument which localizes the point of highest current density in the tissue of the patient at the point where it is most needed to accomplish desiccation and aid in cutting.

It is a still further object of the present invention to provide a bipolar electrosurgical instrument which can accomplish desiccation and cutting without the need for special hand manipulations of the instrument.

It is yet another object of the present invention to provide an electrosurgical instrument which combines graspers and scissors into a single tool.

These and other objects of the present invention will be apparent from the summary and detailed descriptions which follow.

SUMMARY OF THE INVENTION

In a first embodiment, the present invention relates to a bipolar electrosurgical instrument for grasping, desiccating and cutting tissue. The instrument includes four shearing members each of which is provided with a blade member having an electrically conductive portion. The shearing members are pivotally joined whereby the blade members are positioned such that two of the blade members form an upper blade pair, two of the blade members form a lower blade pair and the electrically conductive portions of the upper blade pair opposes the electrically conductive portions of the lower blade pair. The instrument further includes a means coupled to the shearing members for moving the upper and lower blade pairs relative to one another to the open and closed positions and for moving lateral pairs of the blade members relative to one another in order to cut tissue using the blade members. The instrument also includes a means for applying voltage across the electrically conductive portions of the blade members.

In a second embodiment, the present invention relates to a method of using a bipolar electrosurgical instrument to grasp, desiccate and mechanically sever tissue. The method includes the steps of providing a bipolar electrosurgical instrument as described above, opening the blade members, closing the blade members on tissue to thereby make electrical contact with the tissue, applying a voltage across the electrically conductive portions of the blade members and subsequently moving one lateral pair of blade members with respect to the other lateral pair of blade members to thereby cut the tissue.

In a further embodiment of the present invention, the voltage is applied across the blade members in a diagonal pattern to thereby localize the current to a very small area of tissue in contact with the blade members. This diagonal pattern minimizes damage to adjacent tissue which can occur as a result of the application of voltage using the electrosurgical instrument.

DETAILED DESCRIPTION OF THE PREFERRED EMBODIMENTS

Referring now to the figures like elements are represented by like numerals throughout the several views.

Figure 1:
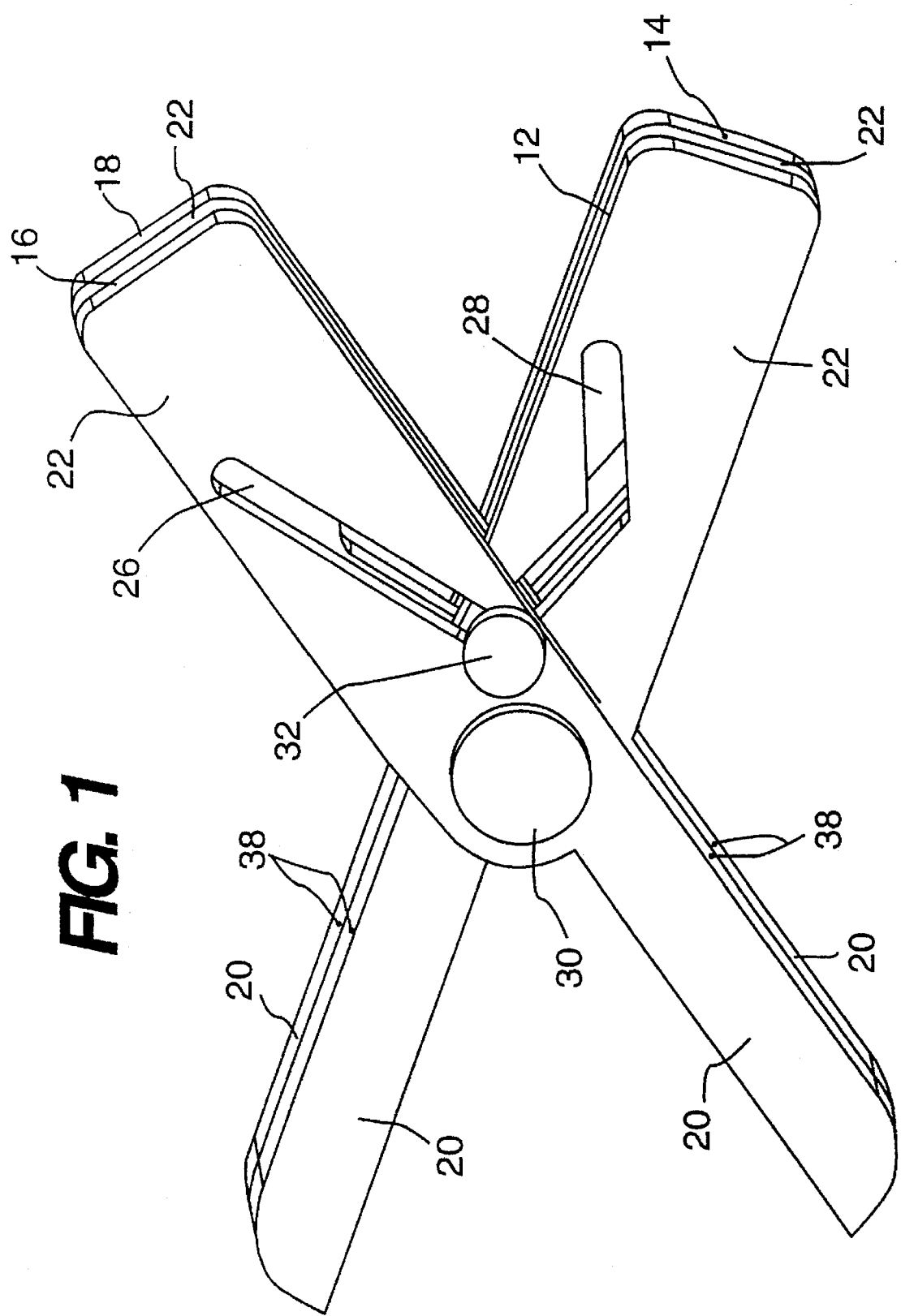
FIG. 1 is a top elevational view of one embodiment of the shearing members in the open position.

In FIG. 1 there is shown the four shearing members of the electrosurgical instrument 10 of the present invention. In particular, the upper pair of shearing members comprises first shearing member 12 and second shearing member 14. The lower pair of shearing members comprises third shearing member 16 and fourth shearing member 18. Each of the shearing members 12, 14, 16, 18 are divided into blade members 20 and support members 22.

Support members 22 are affixed to one another by pivot pin 30 which is located in a pivot hole 31 which penetrates each support member 22. Other conventional means for pivotal attachment, such as pivotable linkage, may also be employed. Each support member 22 also includes a slot with particular support members 22 having a linear slot 26 and other support members 22 having a V-shaped slot 28. Located in linear slots 26 and V-shaped slots 28 is a slider pin 32 which is adapted to slide along the length of linear slots 26 and V-shaped slots 28 to cause movement of shearing members 12, 14, 16, 18 relative to one another.

To the back side of blade members 20 are connected electrical contacts 38 for application of voltage to blade members 20. In particular, small holes are drilled in the back of blade members 20 and a pin is inserted and welded into the holes and soldered with a wire to thereby make the four electrical connections 38.

In FIG. 1 the blade members 20 are shown in the open position which is employed for positioning the electrosurgical instrument 10 with respect to the tissue to be desiccated and cut. Thus, the tissue is placed between the upper pair of blade members 20 and the lower pair of blade members 20 with the electrosurgical instrument 10 in the open position shown in FIG. 1.

Figure 2:
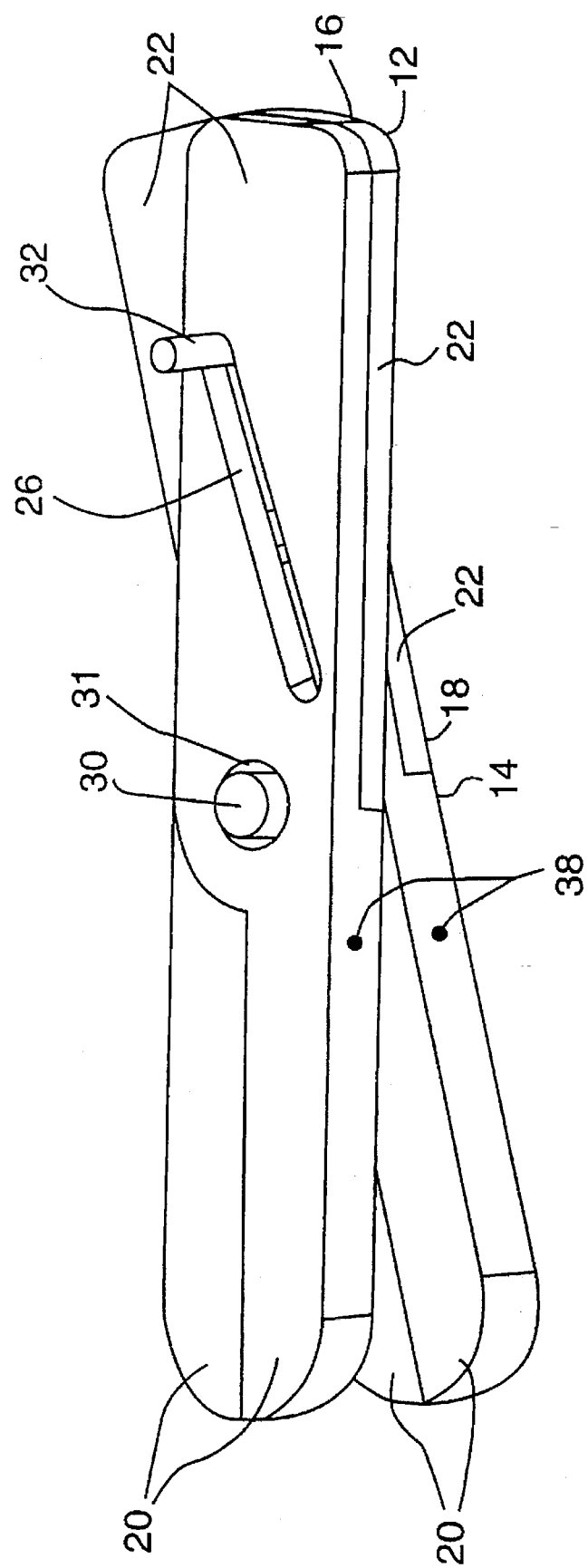
FIG. 2 is a side elevational view of the shearing members in the position reached when cutting is complete.

Referring now to FIG. 2 there is shown the shearing members 12, 14, 16, 18 in the position reached after cutting whereby one lateral pair of shearing members 12, 16 moves across the other lateral pair of shearing members 14, 18 to thereby cut the tissue located between the blade members 20.

Figure 3:
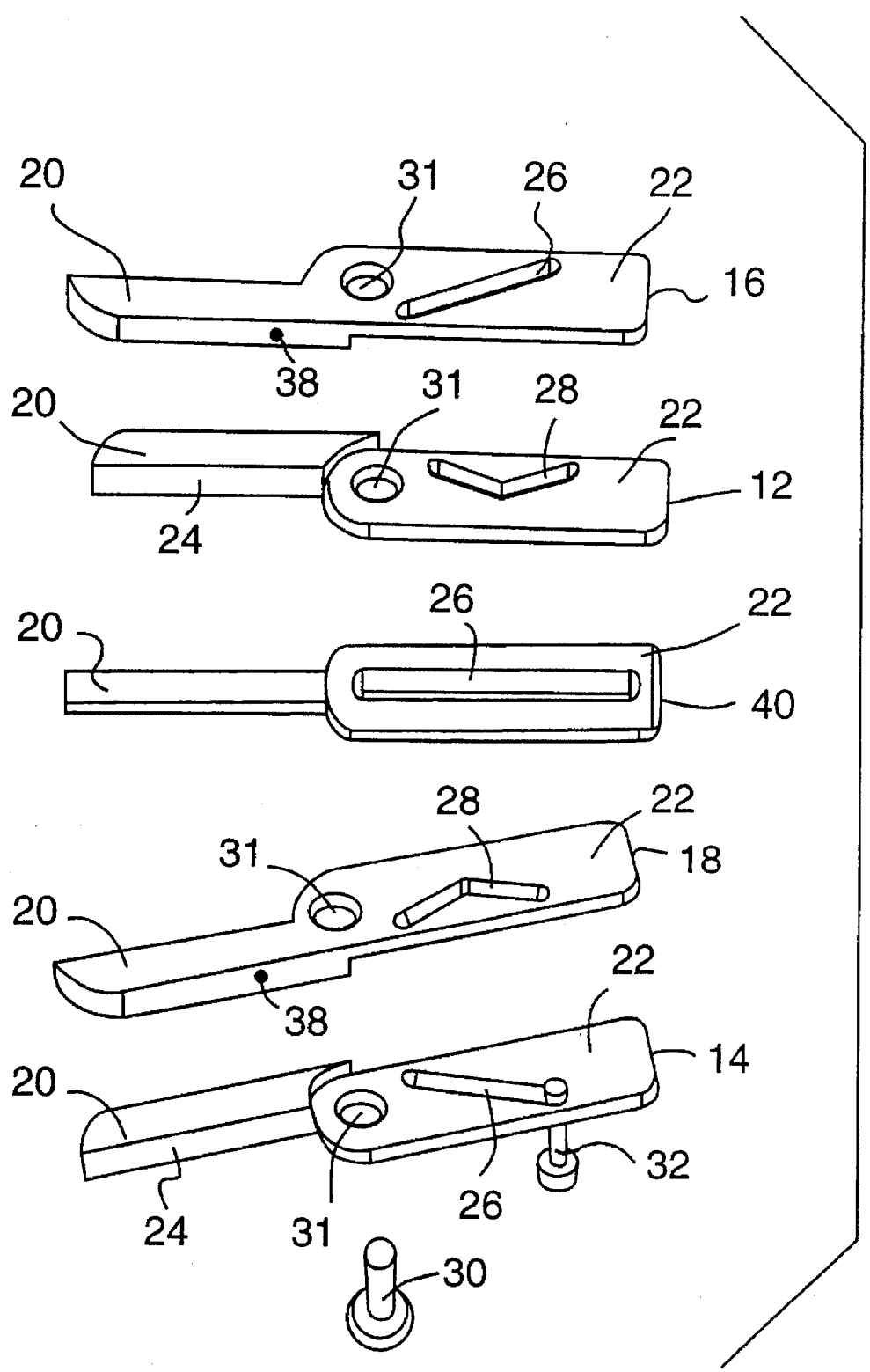
FIG. 3 is an exploded view of the shearing members of the instrument of the present invention.

In FIG. 3 there is shown an exploded view of shearing members 12, 14, 16, 18 of the invention. Support members 22 of shearing members 14, 16 comprise linear slots 26 whereas support members 22 of shearing members 12, 18 comprise V-shaped slots 28. By movement within linear slots 26 and V-shaped slots 28, slider pin 32 imparts the appropriate motion to each of the shearing members 12, 14, 16, 18 for opening, closing and cutting using the electrosurgical instrument 10.

The optional, fifth shearing member 40 of the invention is also shown. Fifth shearing member 40 is mounted on pivot pin 30 for reciprocating movement between the blade members 20 of lateral pairs of shearing members and can be employed instead of, or in addition to the cutting step in order cut the tissue after desiccation.

Also shown in FIG. 3 is the pivot hole 31 which penetrates each support 22 of shearing members 12, 14, 16, 18. Pivot hole 31 is adapted to receive pivot pin 30 about which all four shearing members 12, 14, 16, 18 are pivotally movable.

Finally, FIG. 3 also shows electrically conductive portions 24 of blade members 20 of shearing members 12, 14. Blade members 20 of shearing members 16, 18 contain similar electrically conductive portions 24 (not shown) on the cutting surface of blade members 20.

The preferred means for imparting electrical conductivity to the electrosurgical instrument 10 is to machine shearing members 12, 14, 16, 18 from a conductive alloy. Shearing members 12, 14, 16, 18 are then anodized, preferably to impart a dielectric strength of about 9–10 kV/mm on the surface thereof. In a preferred embodiment, the anodization process combines alumina with teflon to thereby impart an insulative layer with stick resistance to the surface of the shearing members 12, 14, 16, 18. The thickness of the anodized layer is preferably about 50–100 µm.

The anodization process electrically insulates the surface of shearing members 12, 14, 16, 18. The cutting edges of blade members 20 may then be selectively ground to remove the anodized layer and create electrically conductive portions 24 on the surface of blade members 20 for conducting electrical current into the tissue to be desiccated. The electrical contacts 38 are made to the back side of shearing members 12, 14, 16, 18 by drilling small holes through the anodized layer into blade members 20 and inserting and welding a conductive pin in the holes. In operation, the electrosurgical instrument 10, when in the closed position, will contact the tissue via electrically conductive portions 24.

Figure 4:
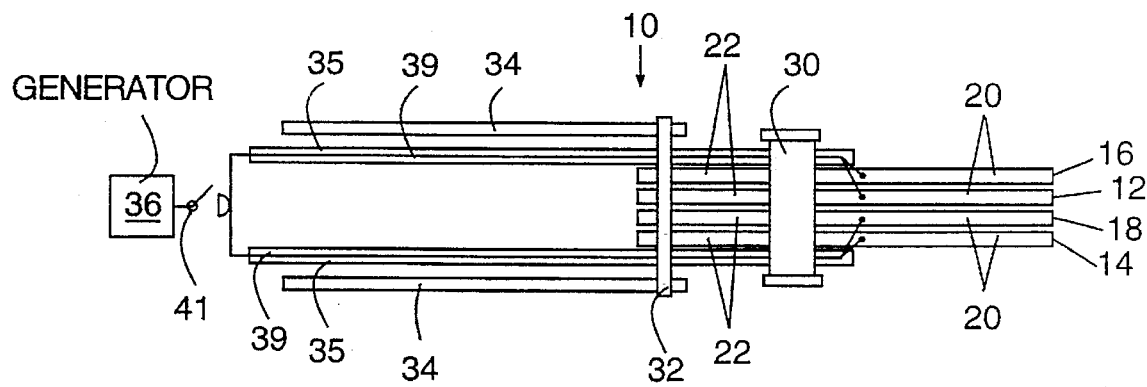
FIG. 4 is a cross-sectional side view of the electrosurgical instrument of the present invention.

FIG. 4 shows one embodiment of the electrosurgical instrument 10 of the present invention in cross-section. In this view it can be seen that shearing members 12, 14, 16, 18 are located above one another and are held together by pivot pin 30. This embodiment employs handles 35 which are attached to support members 22 via pivot pin 30 and provide a means for gripping the apparatus. In addition, the handles 35 include electrical wires 39 therein. Each handle 35 comprises two electrical wires 39 such that there is a single electrical wire 39 for each shearing member 12, 14, 16, 18. Electrical wires 39 are connected to the back side of blade members 20 as described above and run through or along handles 35 via a switch 41 to electrical generator 36 (shown schematically). Any suitable means of applying a voltage across the blade members may be employed such as a generator, batteries, or other electrical generation apparatus known in the art.

Reciprocating linkages 34 are connected to slider pin 32. Reciprocating linkages 34 impart a reciprocating motion to slider pin 32 to thereby move slider pin 32 along the lengths of linear slots 26 and V-shaped slots 28 to cause motion of shearing members 12, 14, 16, 18.

Figure 5:
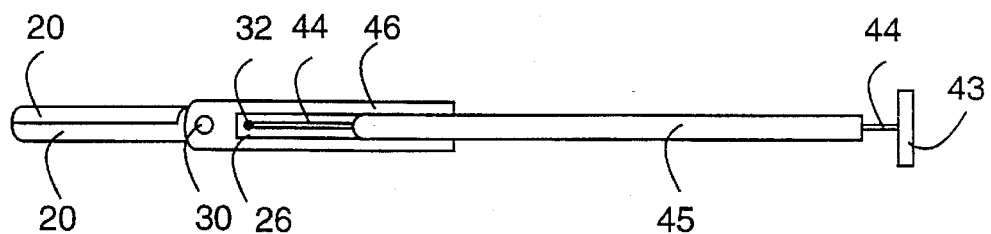
FIG. 5 is a bottom plan view of a second embodiment of the present invention.

Referring to FIG. 5 there is shown a bottom plan view of an alternative embodiment of the present invention to that shown in FIG. 4. This embodiment employs a handle 45 through which a single reciprocating member 44 passes to a grip 43 as shown in the Figure. The single reciprocating member 44 is mounted for reciprocating movement within handle 45 and is actuated by pushing and pulling on grip 43.

Reciprocating member 44 is connected to slider pin 32 which rides in linear slots 26 and V-shaped slots 28 as in previous embodiments. Handle 45 includes a plate 46 to which shearing members 12, 14, 16, 18 are affixed via pivot pin 30. Plate 46 additional reinforcement to provide structural stability to the electrosurgical instrument 10.

Shearing members 12, 14, 16, 18 are attached below plate 46 and thus only two blade members 20 can be seen in FIG. 5. However the structure of shearing members 12, 14, 16, 18, blade members 20 and support members 22 in the embodiment in FIG. 5 is the same as the structure of shearing members 12, 14, 16, 18 shown in FIGS. 1-2. Blade members 20 in FIG. 5 are shown in the closed position which position is employed for desiccation of tissue by application of voltage across the conductive portions 24 (not shown) of the blade members 20. The electrical contacts and generator are not shown in FIG. 5 and are substantially the same as those shown in FIG. 4.

Figure 6A:
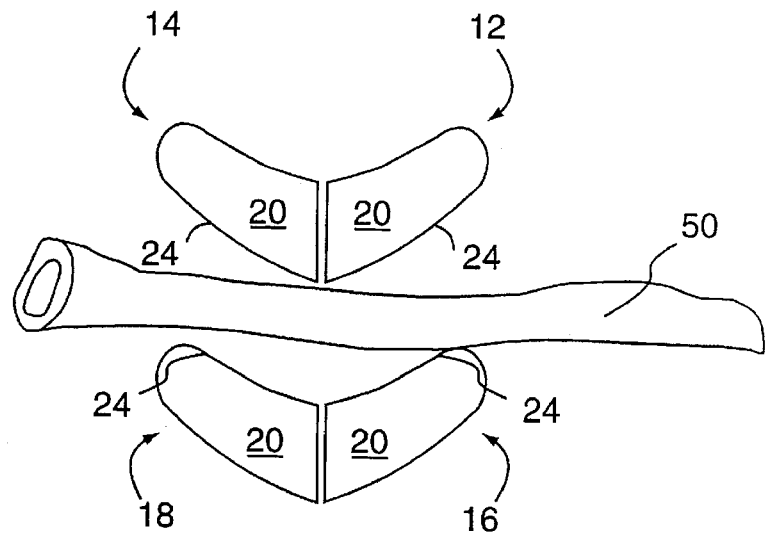
FIG. 6a is a schematic representation of the first step of tissue cutting operation employing the elctrosurgical instrument of the present invention wherein the instrument is opened and the tissue is placed between the top and bottom blades.
Figure 6B:
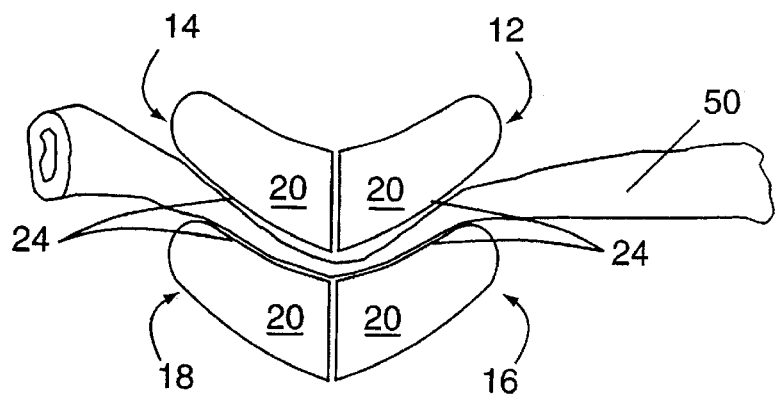
FIG. 6b is a schematic representation of the second step of a tissue cutting operation employing the electrosurgical instrument of the present invention wherein the blades are closed and the tissue is desiccated by applying current.
Figure 6C:
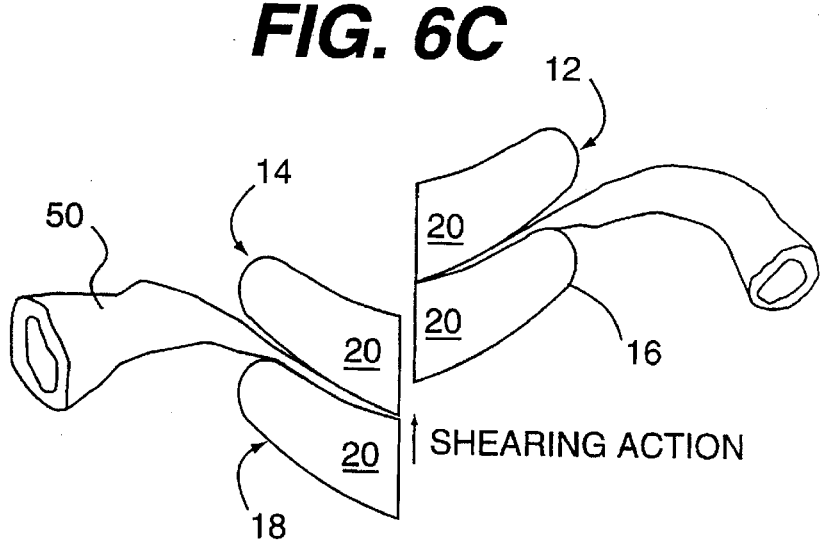
FIG. 6c is a schematic representation of step 3 of a tissue cutting operation employing the electrosurgical instrument of the present invention wherein the tissue is cut by shearing the two lateral blades.

Referring now to FIG. 6 the method of operation of the electrosurgical instrument 10 of the invention is demonstrated using an end view of blade members 20. In the first step of the method of operation of electrosurgical instrument 10 blade members 20 are opened to the open position shown in step 1 of FIG. 6 (and in FIG. 1) and tissue 50 is inserted between blade members 20 of upper shearing members 12, 14 and blade members 20 of lower shearing members 16, 18. As shown in FIG. 1 slider pin 32 is positioned at the forwardmost point in linear slots 26 and V-shaped slots 28 when shearing members 12, 14, 16, 18 are in the open position.

The second step of the operation of the electrosurgical instrument 10 involves moving reciprocating linkage 34 to slide slider pin 32 along linear slots 26 and V-shaped slots 28 to a point approximately halfway along slots 26, 28 as shown in FIG. 5, whereby blade members 20 move to the closed position, as shown in step 2 of FIG. 6. In the closed position, the electrically conductive portions 24 contact the tissue 50. While blade members 20 are in this position of step 2, voltage is applied across the electrically conductive portions 24 of blade members 20 to desiccate the tissue 50.

The voltage may be applied in one of several ways. For example, it is possible to apply the voltage simultaneously between shearing members 12, 14 and shearing members 16, 18. It is also possible to apply voltage across shearing members 12 and 16 and then subsequently apply voltage across shearing members 14 and 18.

In the most preferred embodiment of the present invention, voltage is applied sequentially across diagonal pairs of shearing members. For example, voltage is first applied across shearing members 12 and 18, and then applied across shearing members 14 and 16. In this manner, an x-shaped pattern of current flow is obtained which localizes the current flow through tissue 50 to a very small area thereby minimizing trauma and heat damage to surrounding tissue.

The final step in the operation of the electrosurgical instrument 10 is the shearing action. The shearing action is accomplished by further moving the reciprocating linkage 34 to cause slider pin 32 to slide all the way to the end of slots 26 and 28 to thereby move lateral pair of shearing members 12, 16 across lateral pair of shearing members 14, 18 as shown in step 3 of FIG. 6 ultimately arriving at position shown in FIG. 2. The V-shaped slots 28 in supports 22 of shearing members 12, 18 change the direction of motion of shearing members 12, 18 once slider pin 32 reaches the halfway point in the V-shaped slots 28 in order to provide the shearing action. In this relatively simple mechanical fashion a complex motion of the shearing members 12, 14, 16, 18 is achieved by the present invention.

Alternative means for imparting the desired complex sequence of movements employ a single shaft which imparts a linear push/pull force to the tip. The linear force is converted to the complex sequence of blade movements using discontinuous cam/slider combinations at the end of the shaft.

Optionally, mechanical and/or electronic means such as switch 41 shown in FIG. 4 may be provided to shut off the electric current from generator 36 during cutting in order to prevent electrical shorting. Such means may be an automatic shut off means which is triggered by the position by the reciprocating linkage 34, slider pin 32 and/or shearing members 12, 14, 16, 18. A separate on/off switch can be provided for actuation by the surgeon in order to apply the voltage when desired. Each application of voltage typically has a duration of about 0.1 seconds or less since this will be sufficient to desiccate the extremely localized area of tissue that will be affected by the instrument of the present invention.

Blade members 20 are typically made from stainless steel, aluminum or any other conductive metal. The metal is then anodized to provide an insulative coating thereon and the insulative coating is selectively removed to create electrically conductive portions 24 on the surface of the blade members 20. Stick resistant coatings can optionally be applied over the entire assembly to improve performance and can be combined with the anodization process to provide a stick resistant insulative coating by, for example, anodizing with a combination of alumina and teflon.

The present invention solves several difficult problems encountered by such bipolar electrosurgical instruments. For example, in many instruments the electrically insulative material must be bonded to an electrically conductive material in order to fabricate the instrument. The present invention, however, does not require this bonding and thereby eliminates a difficult manufacturing step as well as a major cause of failure of such instruments due to the debonding of the insulative material from the conductive material. Further, no brittle, insulative, ceramic materials are required in the instruments of the present invention and thus the problems associated with shattering of these ceramic materials are eliminated.

Another major problem solved by the instrument of the present invention is related to the requirement that bipolar scissors depend on a slight radial mismatch between the mating blades to sustain a good shearing edge. Thus, tight tolerances are needed when fabricating the blades in order to induce a spring force between the blades and thereby obtain a good shearing action. With ceramics, it is very hard to obtain such tight tolerances since ceramics are typically molded and subsequently fired whereby shrinking occurs thereby changing the shape of the material.

Another problem with ceramics is surface roughness. Metal surfaces, in comparison, can easily be polished to obtain a very smooth surface which does not have a "gritty" feel during cutting as do many commercially available bipolar scissors.

Finally, when as in many commercially available electrosurgical instruments, the two mating blades are separated by layer(s) of insulative material, tissue desiccation can only be accomplished by manipulation of the instrument to position the tissue between the conductive portions of the blade. Typically, such manipulation involves rotation of the surgeon's wrist to position the tissue in electrical contact with the exterior conducting portions of the blade members, activation of an electrical switch to desiccate and subsequent rotation of the wrist to the original position before cutting. The present invention, by comparison, eliminates the need for this complicated manipulation of the instrument by the surgeon.

It is considered that the present invention represents a substantial advancement in the art. The present invention will be further illustrated by the following examples.

EXAMPLES 1–3

The electrosurgical instrument shown in FIG. 5 of the present application was tested both with, and without application of electrical current to cut fatty chicken tissue. Application of electrical current was accomplished using an Aspen Excalibur surgical generator set at the bipolar setting. The prototype instrument was further tested on an anesthetized pig. In this test, small blood vessels were desiccated and subsequently cut using the prototype scissors and any bleeding from the site was observed.

The performance of the electrosurgical instrument of the present invention was similar to or better than other types of bipolar scissors for cutting both and live and non-living tissue with or without application of electrical current. No bleeding was observed when live small blood vessels were desiccated and cut. The scissors were easy and inexpensive to manufacture since there was no need to bond dissimilar materials to one another. Also, no hand manipulations were required to position the scissors for desiccation and/or cutting.

The foregoing examples were presented for the purpose of illustration and description only and are not to be construed as limiting the invention in any way. The scope of the invention is to be determined from the claims appended hereto.

What is claimed is:

1. A bipolar electrosurgical instrument for grasping, cutting and desiccating tissue which comprises:
   (a) four shearing members each provided with a blade member having an electrically conductive portion;
   (b) means for pivotally joining said shearing members whereby the blade members are positioned such that two of said blade members form an upper blade pair, the other two of said blade members form a lower blade pair, and the electrically conductive portions of said upper blade pair opposes the electrically conductive portions of said lower blade pair;
   (c) means coupled to said shearing members for pivotally moving said upper and lower blade pairs relative to one another to respective open and closed positions, and for moving lateral pairs of said blade members relative to one another in order to cut tissue using said blade members; and
   (d) means for applying a voltage across said electrically conductive portions of said blade members.

2. A bipolar electrosurgical instrument as claimed in claim 1 wherein each of said shearing members further comprises a support attached to said blade member and wherein the means for pivotally joining said shearing members is attached to the support of each of said shearing members.

3. A bipolar electrosurgical instrument as claimed in claim 2 wherein said means for pivotally moving of said blade pairs comprises a slot located in each of the supports of said shearing members, a slider pin positioned for reciprocating movement within said slots, and a reciprocating linkage connected to said slider pin for imparting reciprocating movement thereto.

4. A bipolar electrosurgical instrument as claimed in claim 3 wherein one of said shearing members which forms said upper blade pair and one of said shearing members which forms said lower blade pair comprise a linear slot and the other of said shearing members which form said upper and lower blade pairs comprise a V-shaped slot.

5. A bipolar electrosurgical instrument as claimed in claim 2 wherein said means for applying voltage applies said voltage across the electrically conductive portions of respective pairs of said blade members.

6. A bipolar electrosurgical instrument as claimed in claim 5 wherein said means for applying voltage applies voltage across the electrically conductive portions of lateral pairs of said blade members.

7. A bipolar electrosurgical instrument as claimed in claim 6, wherein said means for applying voltage applies voltage sequentially, first across the electrically conductive portions of a first, diagonal pair of said blade members and subsequently across the electrically conductive portions of a second, diagonal pair of said blade members.

8. A bipolar electrosurgical instrument as claimed in claim 6 further comprising a means for discontinuing the application of voltage during the cutting motion of said shearing members.

9. A bipolar electrosurgical instrument as claimed in claim 1 further comprising a fifth shearing member affixed to said means for pivotally joining said shearing members and adapted for linear, reciprocating movement.

10. A bipolar electrosurgical instrument as claimed in claim 1 wherein said means for pivotally joining said shearing members comprises a pivot pin.

11. A bipolar electrosurgical instrument as claimed in claim 1 wherein the shearing members comprise an electrically insulative coating which is selectively removed from portions of the blade members to create the electrically conductive portions of said blade members.

12. A method of using a bipolar electrosurgical instrument to grasp, desiccate and mechanically sever tissue, said method comprising the steps of:
   a) providing a bipolar electrosurgical instrument comprising four shearing members each provided with a blade member having an electrically conductive portion, means for pivotally joining said shearing members with the electrically conductive portions of upper and lower pairs of said blade members opposing one another, means coupled to said shearing members for imparting movement of pairs of said blade members relative to one another for opening and closing said blade members and for cutting tissue using said blade members; and means for applying a voltage across said electrically conductive portions of said blade members;

b) opening said blade members;

c) closing the blade members on tissue to thereby make electrical contact between said electrically conductive portions of said blade members and the tissue;

d) applying a voltage across the electrically conductive portions of said blade members; and subsequently e) moving one lateral pair of said blade members with respect to the other lateral pair of said blade members to thereby cut the tissue.

13. A method in accordance with claim 12 wherein said step of applying voltage comprises the steps of:

applying voltage across a first diagonally opposed pair of said electrically conductive portions of said blade members, and subsequently applying voltage across a second diagonally opposed pair of electrically conductive portions of said blade members.

* * * * *